US011351316B2

(12) United States Patent
Von Schuckmann (10) Patent No.: US 11,351,316 B2
(45) Date of Patent: Jun. 7, 2022

(54) HANDHELD DEVICE FOR DISPENSING OF A PHARMACEUTICAL SUBSTANCE AND COUNTER FOR SUCH HANDHELD DEVICE

(71) Applicant: Alfred Von Schuckmann, Kevelaer (DE)

(72) Inventor: Alfred Von Schuckmann, Kevelaer (DE)

(*) Notice: Subject to any disclaimer, the term of this patent is extended or adjusted under 35 U.S.C. 154(b) by 178 days.

(21) Appl. No.: 16/301,543

(22) PCT Filed: Apr. 5, 2017

(86) PCT No.: PCT/EP2017/058063
§ 371 (c)(1),
(2) Date: Nov. 14, 2018

(87) PCT Pub. No.: WO2017/178294
PCT Pub. Date: Oct. 19, 2017

(65) Prior Publication Data
US 2019/0201641 A1 Jul. 4, 2019

(30) Foreign Application Priority Data
Apr. 13, 2016 (DE) .................... 10 2016 106 875.6

(51) Int. Cl.
*A61M 15/00* (2006.01)
*G06M 1/08* (2006.01)
(Continued)

(52) U.S. Cl.
CPC .... *A61M 15/0073* (2014.02); *A61M 15/0025* (2014.02); *G06M 1/00* (2013.01);
(Continued)

(58) Field of Classification Search
CPC .... A61M 15/00; A61M 15/0001–0051; A61M 15/0056; A61M 15/006;
(Continued)

(56) References Cited

U.S. PATENT DOCUMENTS 5,349,945 A * 9/1994 Wass ................... A61M 15/009
128/200.14
6,082,358 A * 7/2000 Scarrott ............ A61M 15/0065
128/200.14
(Continued)

FOREIGN PATENT DOCUMENTS

WO 92/09324 A1 6/1992
WO 2006/051073 A1 5/2006
(Continued)

OTHER PUBLICATIONS

International Search Report of PCT/EP2017/058063, dated Jun. 21, 2017.

*Primary Examiner* — Victoria Murphy
*Assistant Examiner* — Ned T Heffner
(74) *Attorney, Agent, or Firm* — Collard & Roe, P.C.

(57) ABSTRACT

A handheld device for dispensing a pharmaceutical substance has a housing in which a storage container with the pharmaceutical substance and a counter are arranged. The storage container dispenses the pharmaceutical substance by pressure actuation by a user after a specified displacement path has been traversed, and the counter carries out an action in order to rotate a counter wheel of the counter on the basis of the displacement path being traversed. The counter additionally has a drive part rotates the counter wheel, and the counter wheel is rotatably attached to a mounting part. The mounting part is formed independently of the housing, and the drive part is directly attached to the mounting part. The handheld device advantageously dispenses a pharmaceutical substance in that the action is first carried out on the counter wheel of the counter upon the pressure actuation, and the pharmaceutical substance is then dispensed.

3 Claims, 9 Drawing Sheets

(51) Int. Cl.
*G06M 1/24* (2006.01)
*G06M 1/00* (2006.01)

(52) U.S. Cl.
CPC ............ *G06M 1/083* (2013.01); *G06M 1/241* (2013.01); *A61M 15/009* (2013.01); *A61M 15/0021* (2014.02); *A61M 2202/064* (2013.01)

(58) Field of Classification Search
CPC ........... A61M 15/0065; A61M 15/0068–0098; A61M 11/00; G06M 1/00; G06M 1/02–028; G06M 1/086; G06M 1/10–385
See application file for complete search history.

(56) References Cited

U.S. PATENT DOCUMENTS

| | | | |
|---|---|---|---|
| 6,679,251 | B1 | 1/2004 | Gallem et al. |
| 7,448,342 | B2 | 11/2008 | Von Schuckmann |
| 8,132,565 | B2 | 3/2012 | Von Schuckmann |
| 8,474,447 | B2 | 7/2013 | Von Schuckmann et al. |
| 2010/0065649 | A1 | 3/2010 | Bowman et al. |
| 2010/0218759 | A1* | 9/2010 | Anderson ......... A61M 15/0075 128/200.23 |
| 2010/0229855 | A1 | 9/2010 | Howgill |

FOREIGN PATENT DOCUMENTS

| | | |
|---|---|---|
| WO | 2007/104694 A1 | 9/2007 |
| WO | 2009/037085 A1 | 3/2009 |
| WO | 2015/006292 A1 | 1/2015 |
| WO | 2015/153624 A1 | 10/2015 |

\* cited by examiner

Fig. 1

HANDHELD DEVICE FOR DISPENSING OF A PHARMACEUTICAL SUBSTANCE AND COUNTER FOR SUCH HANDHELD DEVICE

CROSS REFERENCE TO RELATED APPLICATIONS

This application is the National Stage of PCT/EP2017/058063 filed on Apr. 5, 2017, which claims priority under 35 U.S.C. § 119 of German Application No. 10 2016 106 875.6 filed on Apr. 13, 2016, the disclosures of which are incorporated by reference. The international application under PCT article 21(2) was not published in English.

The invention pertains first to a handheld device for dispending a pharmaceutical substance, with a housing in which a receptacle with the pharmaceutical substance and a counter is provided for, wherein the receptacle by pressure activation by a user after going through a pre-determined displacement path, dispenses the pharmaceutical substance and the counter experiences depending on the going through the displacement path an effect for turning of a counter wheel of the counter, wherein the counter further has a drive part for turning the counter wheel and the counter wheel is arranged turnable on a holding part, wherein further the holding part is independent from the housing and the drive part is immediately arranged on the holding part.

Further the invention is concerned with a counter for a handheld device for dispensing a pharmaceutical substance with at least one counter wheel having readable characters and a drive part provided for for turning the counter wheel, wherein the counter has a restoring spring for a back moving after actuation and wherein the restoring spring being separately provided for in view of the driving part has an engagement part for cooperation with the driving part.

Such counters are already known in different variations. Particularly, it is to refer to WO2007/104694 A1 (U.S. Pat. No. 8,132,565 B2).

From this is known a handheld device for dispensing a pharmaceutical substance as well as a counter, which counter is during a specific use case arranged on the upper side of a receptacle (reservoir chamber) of the handheld device, wherein said reservoir chamber contains the pharmaceutical substance. It is acted upon due to a direct pressure actuation by a user. A rotational axis of the drive part is accommodated in two bearing formations that are integrally formed on the inner side of an actuating button such that they protrude downward. The counter wheel is accommodated between the actuating button and the housing wall, both of which respectively also form part of the housing.

Further is to refer as to state of the art also to WO 2006/051073 A1 (U.S. Pat. No. 7,448,342 B2). The counter known from this reference, being able to be in the intended use positioned in a handheld device, is during the intended use positioned underneath a closed receptacle containing the pharmaceutical substance and arranged in the handheld device. It is actuated by pressing the receptacle downward. The counter wheel is accommodated between a lower ring part and an upper housing cover. The drive part is loosely inserted and—initially—acts upon the counter wheel by means of a disk part, as well as by means of a planet wheel.

At the subject of the initially cited publication, the only restoring spring provided is the restoring spring that altogether returns the actuating button and is accommodated between the actuating button and an intermediate bottom of the housing. At the subject of the additionally cited publications, the drive part features springable driving fingers that act upon the disk part. The driving fingers extend with reference to a usual use position of the handheld device starting from a plane across to a central axis of the counter mechanism oblique upwards directed, approximately including an angle of 45° with the plane.

In the state of the art the effect on the counter may occur such that a dispension of substance may have occurred already before a counting. This may be reason for irritation of a user who possibly uses a second time the handheld device based on a not given counting and may such in the given case make a double dosage. This especially in case the counter mechanism has not registered the dispensing of the substance. The counter may also show more substance doses based on this as finally are still present in the receptacle.

SUMMARY OF THE INVENTION

Starting from a state of the art as outlined before, the invention is concerned with the problem to provide an advantageous handheld device as well as a counter for such handheld device for dispensing of a pharmaceutical substance.

A possible solution of the problem is given at a handheld device according to a first invention, wherein is focused on that upon force actuation first there is an effect on the counter wheel of the counter and thereafter the dispensing of the pharmaceutical substance.

By this, one can secure, that the delivery of the substance does not occur without counting. There might be in the given case a situation in which a counting occurs without the delivery of substance or a remarkable amount of substance. An irritation of the user in this respect that he has more substance consumed as actually has been counted, is however practically not to exclude.

The object is further solved with a counter mechanism at which the restoring spring is provided for lever-like and does pivot upon actuation around a pivot axis, wherein in a cross-section, in which a largest distance between the engagement part and the pivot axis is given, the restoring spring has, seen from the counter mechanism, a concave course.

Concerning the cross section it is referred to a cross section along the longitudinal axis in a user position of the counting mechanism in a handheld device, which means a lengthwise cross section, especially on a lengthwise cross section in which the restoring spring is shown with a largest length. The largest distance between the engagement part and the pivot axis of the restoring spring may be referred to a distance measure regarded in extension direction of the longitudinal axis.

Based on this a handheld device is provided for at which during pressure actuation of the receptacle for dispensing a pharmaceutical substance first during the herewith coincident linearly movement of the receptacle container relatively to the housing a counting, which means a further movement of the counting wheel of the counting mechanism, does occur, prior to the pharmaceutical substance will be dispensed from the receptacle and to the outside of the handheld device. The dispensing of the pharmaceutical substance may be coincident with a stop-limited end position with relation to the movability of the receptacle within the housing. In case of such stop-limited end position the counting, which means the put forth of the counting wheel for one unit will take place prior to reaching the stop-limit.

The actuation of the counter wheel in advance of the delivery of the substance is preferably reached by respective design of the counter mechanism, especially in view of the restoring spring associated to the counter mechanism. This restoring spring runs starting from a connecting region of the restoring spring e.g. at the holding part essentially concave, which connection may provide for at once the pivot axis of the restoring spring, viewed from the counting mechanism in direction to the restoring spring). The concave course may be provided for by a circular layout with over the length continuously the same or changing radius. Also the concave course may be composed by a succession of circular line sections of different radius and/or rectilinear running sections. Single circular line sections may seen for themselves been built convex running. In this connection is essential that there is the overall concave course of the restoring spring.

The concave course allows to use advantageously the space being to disposal. It results as well a comparatively big area of the spring, on a bottom resting or close to the bottom extending. Associated to a free end of the spring there may be at the occasion of a movement of the counter mechanism resulting in a down pushing or tensioning of the spring respectively, that there is a certain advanced approach to the counting mechanism. This may of advantage as it is illustrated further down.

In a possible embodiment, the concave course is essentially given by two in the described cross section at least nearly elongated linear sections of a spring arm, which enclose among themselves a dull angle of more than 90° up to 160°. As a whole, there is a restoring spring being in its longitudinal extension lever-like provided for, preferably in the relaxed as well as in the non-relaxed condition.

The engagement part may, as it is also preferred, be provided for on an end side of the restoring spring in the area of a free end of the restoring spring facing away from the pivot axis, further preferred being one piece and materially unified with the restoring spring.

With reference to the cross section the restoring spring runs in the direction of a longitudinal axis below the counter, further preferred between the counter and a bottom of the housing.

The engagement part runs with reference to the cross section preferably in a area of the pressure spring (restoring spring) which is outside of the lowest area of the pressure spring. The lowest area of the pressure spring may be, as it is also preferred, the connection area of the spring arm sections including the before mentioned dull angle, over which lowest spring section a support of the restoring spring may be reached on a housing section, for example the housing bottom.

In the use position such is a seesaw-like lever effect in the area of the restoring spring reachable. A down movement of the counter in the course of a respective shift of the receptacle within the housing results due to respective engagement of the pressure spring and the pivoting combined therewith of the spring around its pivot axis at the occasion of support on the housing bottom to a raising of the engagement part against the moving direction of the receptacle and the counter. By this, in a preferred embodiment, not only the drive part is shifted at the occasion of a down shifting of the receptacle and the counter mechanism in the direction of engagement part but moreover, additionally to this, also the engagement part is raised in the direction of the drive part. By this a advanced, leading counting can be reached prior to a completion of the altogether shifting route of the receptacle for the dispense of the pharmaceutical substance being terminated.

Other characteristics of the invention are respectively described and illustrated below in the description of the figures and the drawings, frequently in their preferred correlation with the already described concepts. However, they may also be significant in correlation with only one or multiple individual characteristics described or graphically illustrated herein or independently or in a different overall concept.

Each of the characteristics disclosed above particularly may also be realized in one of the other respective concepts and all above-described characteristics may even be combined in one object.

The spring area for the seesaw-like design of the restoring spring supporting e.g. on a housing bottom may be the already described connection area of two e.g. in general linearly extending spring arm sections. Also this support area may be given by a partial area of a spring section following a section of a circle line, wherein further during impact on the spring at the occasion of movement of the receptacle and of the counting mechanism, the precise support point on the housing bottom or similar may wander along the concave course to the spring arm, especially in case of a course according to a section of a circular line.

In each case, the linear shift of a section of the restoring spring being combined immediately at the pivot axis on the counter is accompanied by a movement of the restoring spring section which has 'the engagement part but in opposite directions.

The movement way necessary for a proper function of the counting mechanism, relative to the drive part, which corresponds in the state of the art to the total movement way of the receptacle within the housing, is the addition following the present solution from a part of the total movement way of the receptacle with the counting mechanism and the way the engagement part moves resulting from an overlapped movement of the engagement part approaching the drive part.

The restoring spring is preferably also in the non-tensioned condition abutting on the housing, especially on the bottom of the housing of the handheld device.

Especially is also preferred that the blocking part is in one part, further preferred materially unified one part, is provided for already with the holding part. Therewith the holding part has a further function what does attribute to the fact that a counter with a few as possible single parts is provided for.

The counter wheel may be realized cylindrically as already mentioned above and features an engagement toothing, which is preferably realized on a lower peripheral edge during the intended use. Since the engagement toothing is preferably realized on the lower peripheral edge of the preferably cylindrical counter wheel, the remaining (outer) surface (toward the top) can be freely used for applying the readable characters.

The cylindrical design of the counter wheel, in which no additional installation parts are provided for in the interior of the thusly formed cylinder body, is also advantageous with respect to the interaction with a receptacle of the handheld device, in which the pharmaceutical substances accommodated. It is preferred that only sections of the mounting part are located in the interior of the counter wheel. The receptacle is typically realized in the form of a so-called canister, which in a longitudinal cross section has a stepped bottom with a central pin-like projection, wherein a tubular valve part, from which the substance is ultimately discharged during an actuation, protrudes from said projection.

The cylindrical design of the counter wheel particularly may be realized in such a way that an upper end face of the cylinder body can be arranged such that it is assigned to the lower, outer step surface of the aforementioned receptacle.

In order to be actuated by a user, the receptacle typically has to be pressed downward against a spring arranged in the receptacle itself whereby then based on the pressure exertion on the counting wheel or the holding part receiving the counter wheel respectively the movement does occur, which at the end based on the seesaw-like via the spring counter to the moved engagement part triggers the leading actuation of the counter mechanism prior to a dispensing of the pharmaceutical substance.

Similarly, the mounting part is preferably realized cylindrically.

Also the mounting part may overlap the counter wheel from inside in a longitudinal cross section. Consequently, the outer surface of the counter wheel is exposed. This outer surface preferably carries the aforementioned readable characters.

According to another detail, the drive part may preferably be realized in the form of a worm shaft with toothing projections. This means that a circumferential toothing is in fact provided, but this circumferential toothing on the drive part is realized on a helix that extends obliquely to a rotational axis of the drive part and helically around the rotational axis.

The counter wheel is arranged preferably such that its rotational axis extends transverse to a central axis of the counter wheel and/or the mounting part, which is preferably a cylinder axis. Moreover, the rotational axis, as it is also preferred, may be directed parallel to the geometrical pivot axis of the restoring spring.

The engagement part preferably acts upon the drive part on the counter wheel side of the rotational axis of the drive part. The described toothing projections particularly also serve especially for the interaction between the engagement part and the drive part, as well as the blocking part.

The blocking part acts preferably concerning the counting wheel on the inner side of the holding part or the counter wheel side of the rotational axis of the drive part respectively. In this way, the drive part initially is acted upon on opposite sides—referred to the rotational axis of the locking part and the drive part. The aforementioned parts can such move toward one another without any risk of obstruction.

The locking part and the engagement part are preferably arranged such that they are directed oppositely. The free ends of the locking part and the engagement part are arranged such that they are directed toward one another.

In this case, the locking part particularly may be arranged on the upper side and the engagement part may be arranged on the lower side—referred to the described installation state, in which the counter is acted upon by the receptacle from above.

The engagement part and/or the locking part are arranged outside the counter wheel or the mounting part in general—referred to a view from above or below, in which a central axis of the counter wheel and/or the mounting part forms a point. In other respects, the arrangement outside the mounting part refers to the fact that the connection for the engagement part, which—with reference to one embodiment—is realized by the restoring spring itself, or the connection for the locking part, which then insofar also form parts of the mounting part, already are considered as lying outside the mounting part to the extent, to which they are visible in the aforementioned view.

In the aforementioned view, the restoring spring may also laterally extend beyond the engagement part and/or the locking part.

The restoring spring itself is preferably realized in the form of a bow, particularly a closed bow. The bow has two ends that are fastened on the mounting part. The fastening regions, for example in the form of connecting points, may lie approximately opposite of one another referred to a diameter line of the preferably cylindrical mounting part and the cylinder defined by the mounting walls. They may also lie opposite of one another on a secant referred to a thusly formed circle of the cylinder. In the latter instance, the fastening regions or the connecting points respectively are preferably arranged offset to the central axis in such a way that the central axis lies between the secant and the locking part and/or the engagement part, wherein this once again refers, for example, to the view from above, in which the central axis forms a point. The fastening regions or the immediately the fastening regions surrounding areas of the bows on the soring side may give the geometrical pivot axis.

The counter wheel is preferably realized in the form of an integral cylinder part.

SHORT DESCRIPTION OF THE DRAWINGS

The invention is described in greater detail below with reference to the attached drawings that, however, merely show an exemplary embodiment. In these drawings.

DESCRIPTION OF THE EMBODIMENTS

Figure 7:
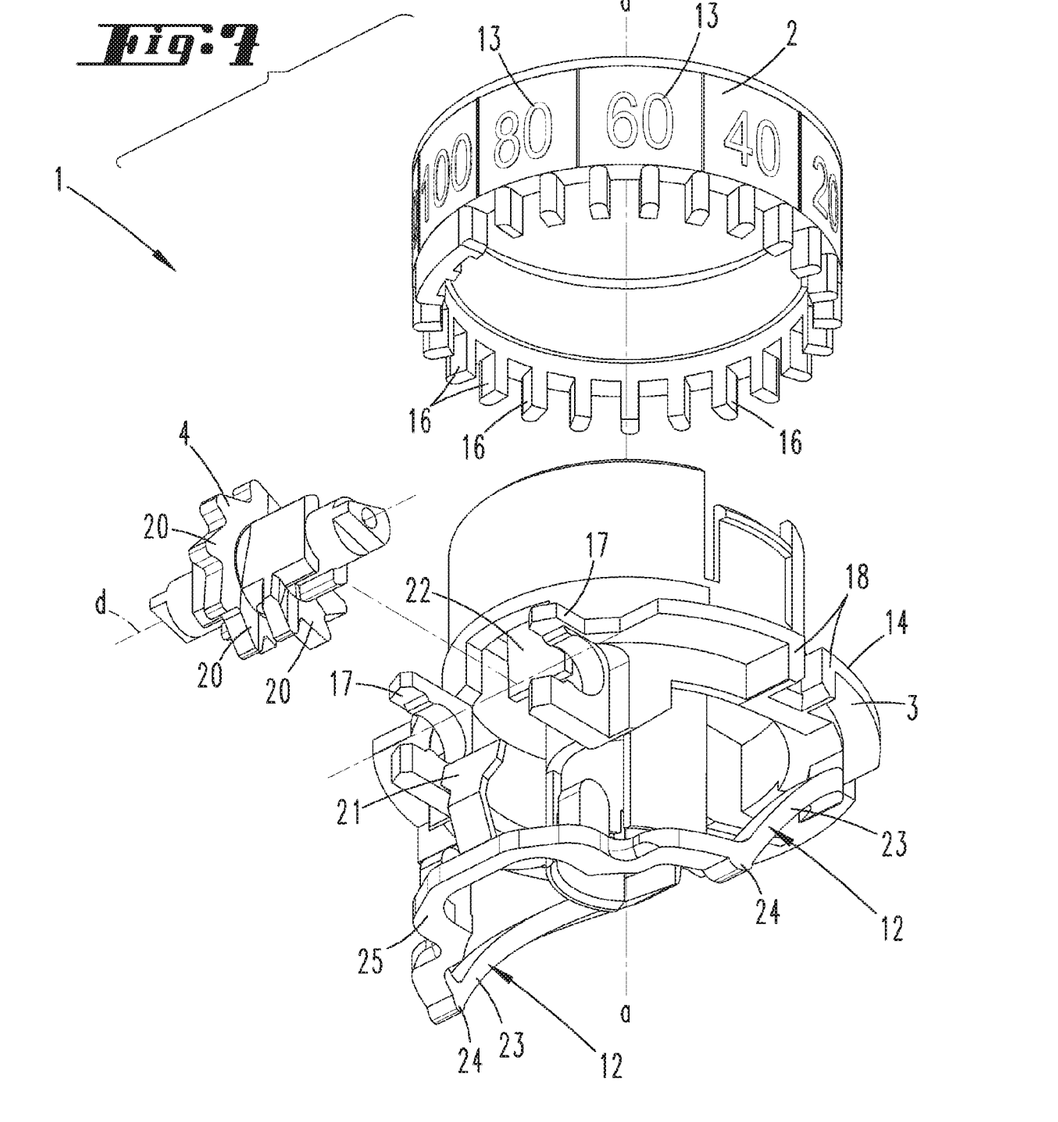
FIG. 7 shows the counter in a perspective explosive view.
Figure 8:
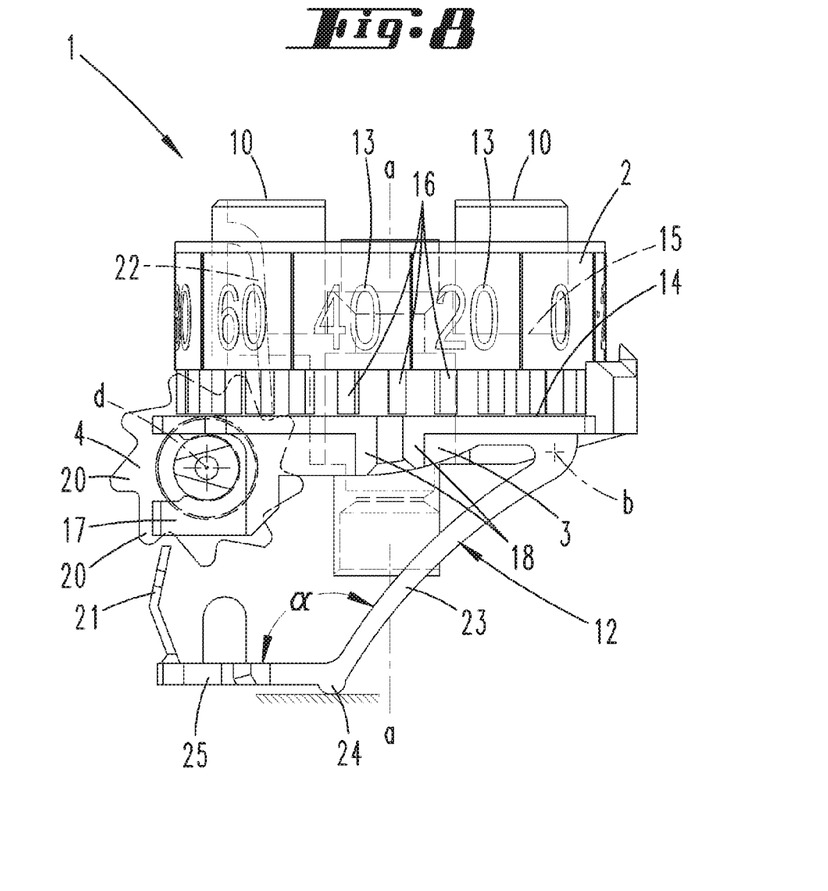
FIG. 8 the counter in an outer view.

Shown and described is, compare especially FIG. 7, a counter 1 composed of a counter wheel 2, a mounting part 3 and a drive part 4.

These few parts, preferably only three parts, are essential to this counter. It is particularly important that the mounting part is realized integrally with additional functions and functional parts, preferably in one piece materially unified.

Figure 1:
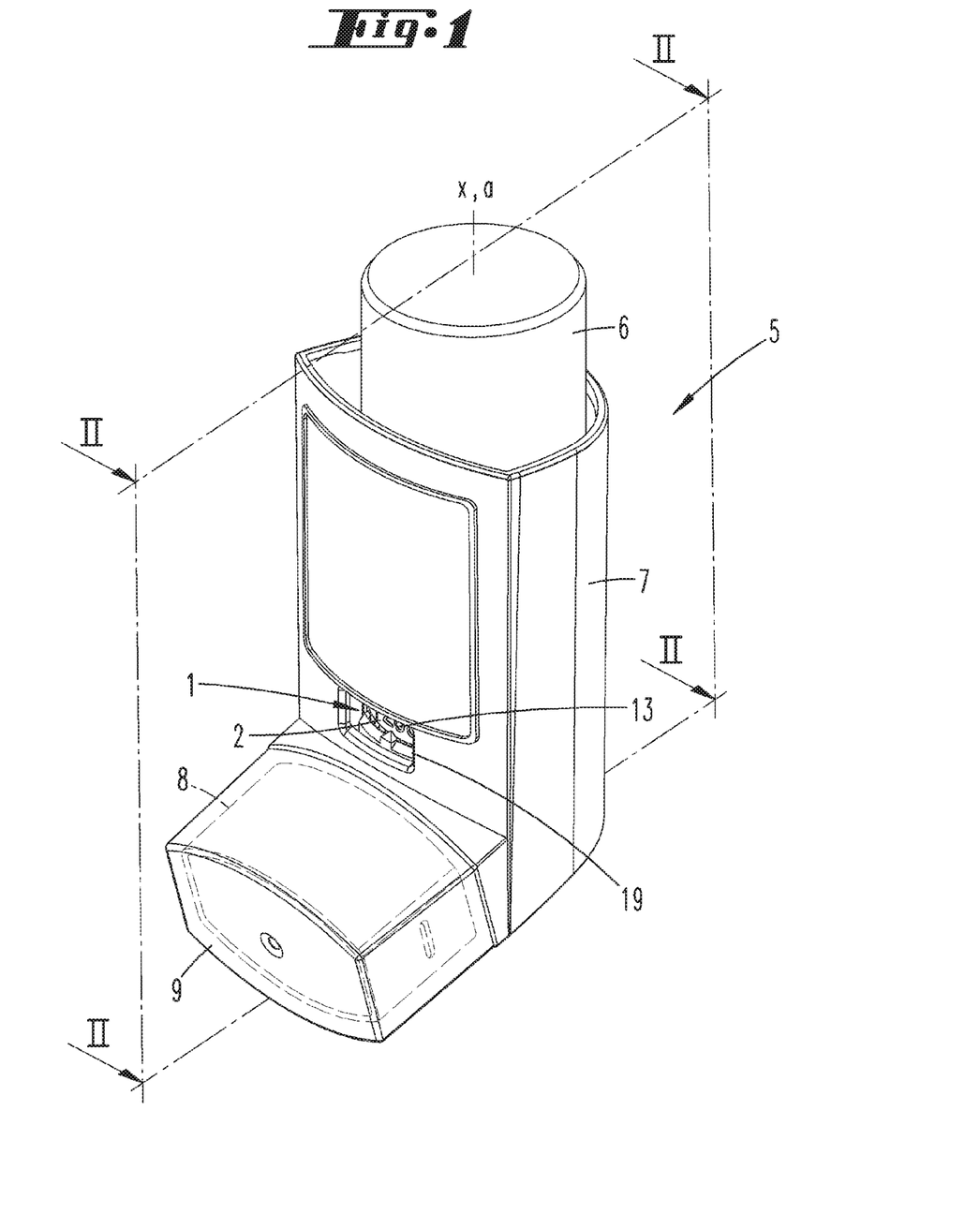
FIG. 1 shows a for example perspective exterior view of an exemplary handheld device with a receptacle arranged therein and a counter.

The counter 1 is arranged in a handheld device 5 of the type illustrated in principle in FIG. 1.

Figure 2:
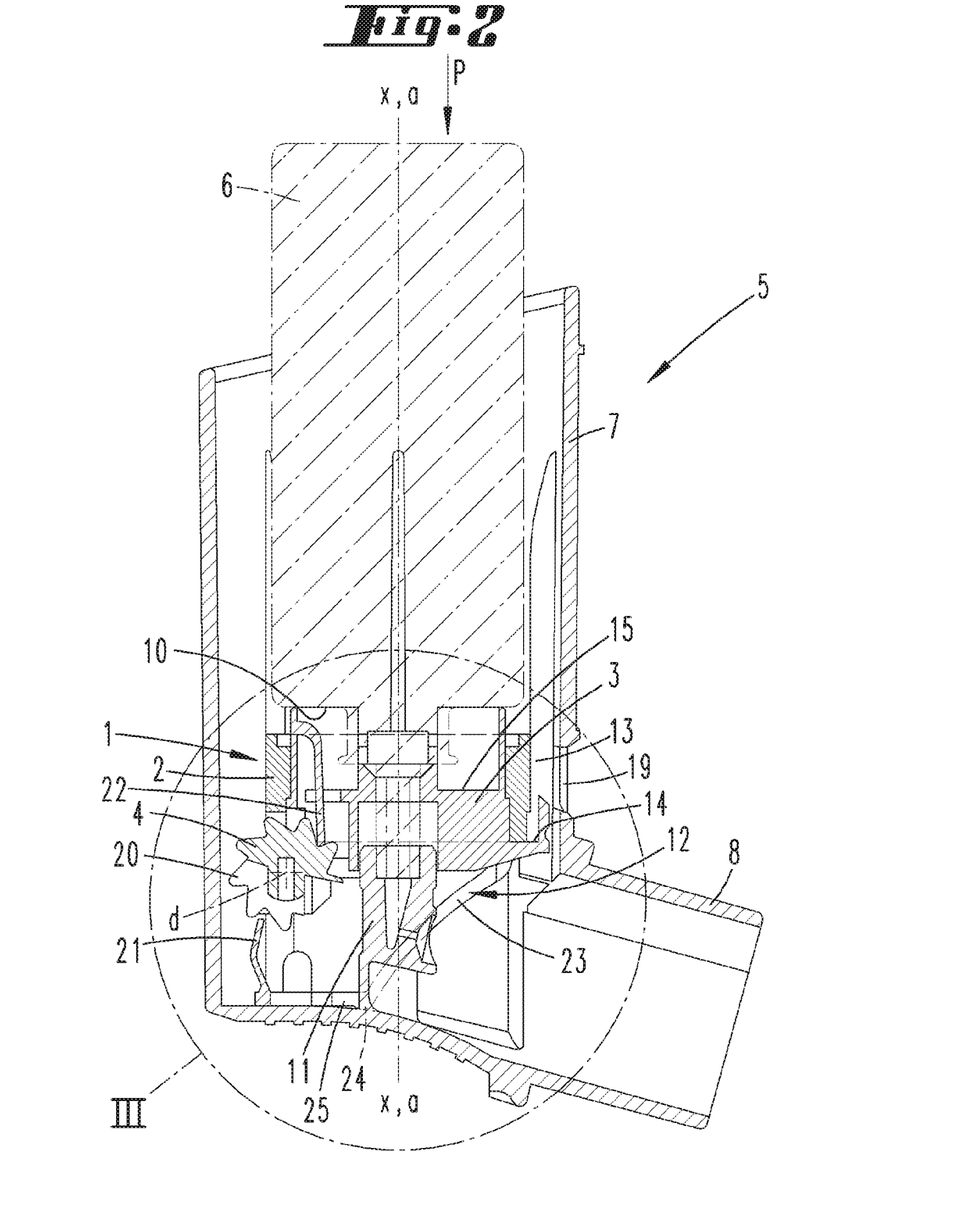
FIG. 2 shows a cross section through the object of FIG. 1 along the plane II-II; concerning an unloaded basic position of the receptacle and the counter mechanism.

The cross section according to FIG. 2 furthermore shows that a receptacle 6 containing the pharmaceutical substance to be dispensed can be arranged in the handheld device 5. The handheld device 5 particularly is an inhalation device.

The handheld device 5 furthermore features a housing 7 that comprises a section, which extends vertically during the intended use and in which a receptacle 6 is accommodated, as well as a mouthpiece 8 that angularly protrudes from this vertical section, e.g. at a right angle or obtuse angle referred to a longitudinal axis x of the vertical section. The mouthpiece 8 may be covered with a cap 9 when the handheld device is not in use.

The entire counter 1 is accommodated in the housing 7 of the handheld device 5.

According to FIG. 2, the counter 1 particularly may be arranged underneath the receptacle 6, the lower side of which is realized in a stepped fashion in a longitudinal cross section, particularly such that the mounting part 3 can come in direct contact with a step surface, preferably an outer step surface 10 of the receptacle 6. The receptacle 6 is actuated by being pressed downward against a not-shown spring that is arranged in the receptacle itself, namely relative to a stationary receiving and dispensing stub 11 in the housing 7.

In this case, the mounting part 3 and the counter wheel 2 accordingly are jointly pressed downward against a restoring spring 12 that is preferably realized on the mounting part as well. While the mounting part and the counter wheel are pressed downward, the drive part 4 interacts with the counter wheel 1 in order to rotationally drive this counter wheel 1 about a central axis a thereof, which may also be a cylinder axis as discussed further below.

The described counter 1 particularly is not designed for individually counting each actuation of the handheld device 5. However, it may also be realized in the form of an individual counter. The counter preferably only displays a new numeral (completely) after a certain number of actuations, for example after 5, 10 or 20 respective actuations.

The counter wheel 2 apparently features corresponding readable characters 13, particularly on an outer circumferential surface of the preferably cylindrical counter wheel 2.

The characters 13 can be read through a window 30 in the housing 7.

The counter wheel 2 is mounted on the mounting part 3. To this end, the mounting part 3 can engage behind the counter wheel 2 with mounting fingers and/or a mounting wall. The mounting fingers may be realized such that they can be elastically deflected. The lower side of the counter wheel 2 may be seated on a step surface 14 of the mounting part 3. The mounting part 3 preferably also features a bottom 15. Furthermore, the bottom 15 preferably features a mounting opening, by means of which the counter 1 may be snap-mounted on the receiving/dispensing stub 11 of the housing 7 in the installed state; see FIG. 2.

Furthermore, the bottom 15 is preferably realized approximately at the height of the step surface 14.

Snap-in fingers may also be realized in the mounting opening in order to promote the potential mounting of the counter on the receiving/dispensing stub 11 of the housing of the device.

To this end, the mounting stub 11 features a circumferential groove, into which such snap-in fingers can engage. In the course of an actuation, the bottom 15 and the counter mechanism 1 can altogether move relative to the housing 7 and especially relative to the receiving/dispensing stub 11 for the vertical height (width) of the groove.

The lower side of the counter wheel 2 is realized with an engagement toothing 16. This engagement tooting makes it possible to act upon the counter mechanism 1 in order to realize its rotation.

The engagement toothing 16 is acted upon by the drive part 4.

The mounting part 3 is preferably also realized toroidal, particularly cylindrical, if applicable with different regions in a vertical direction of a cylinder axis, which preferably coincides with the central axis a. A functional section is preferably provided underneath the step surface 14. This functional section, which preferably also has an annular shape, particularly a cylindrical shape, is provided for with one or more formations that can fulfill one or more functions. A mounting formation 17 is initially provided for mounting the drive part 4. It may consist of snap-in openings for an axis of the drive part 4. Rib-like counter formations 18 for the mounting in the housing 7 of the handheld device 5 are furthermore provided. In addition, the functional section features the connection of the restoring spring 12. This restoring spring may extend from a lower end face of the functional section. Referred to the side view according to FIG. 2, in which the central axis a forms a line and the rotational axis d forms a point, the direction of extent of said restoring spring preferably includes an acute angle with the central axis a. The restoring spring 12 is preferably designed in a bow-like fashion (see FIGS. 6 and 7), particularly such that the bow with its two bow arms is in the aforementioned side view in overlap, so that in cross section or a corresponding view respectively, only the bow arm is visible.

The restoring spring 12 is further preferably concerning the bow-like fashion provided for in a closed way. Two end regions of the bow are preferably on different places underside the holding part 3 as such (which means for this purpose viewed without the restoring spring 12) transforming into this holding part.

Figure 3:
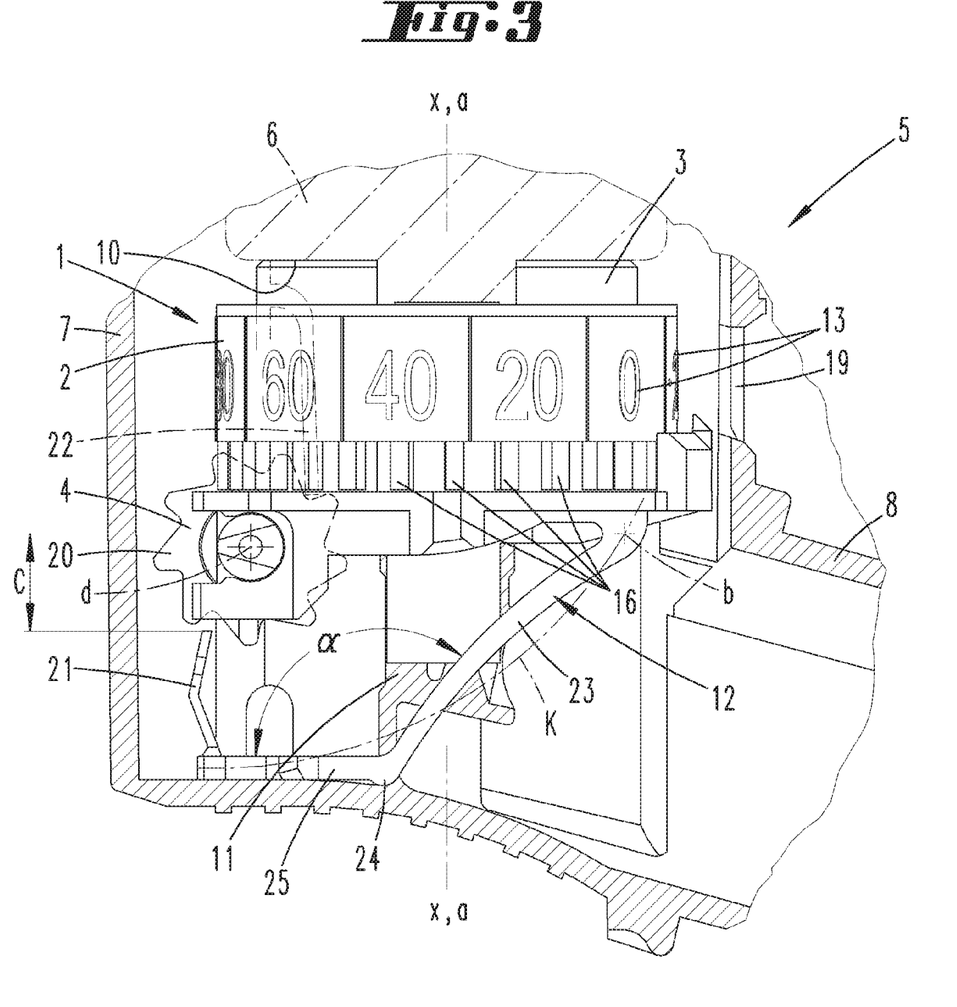
FIG. 3 shows an enlarged detail of the region in FIG. 2, the counter being shown in an outer view.

Altogether there is seen from the counter 1 preferably a concave course K of the restoring spring 12 or bow arms thereof respectively lying overlapping to each other (see FIG. 3). Based on this, starting from the connection region on the functional section, whereby in this connection region a geometrical pivoting axis b is originating, a spring arm section 23 may result which in a section view is nearly running straight up to a section of a circular line inwards in direction to the enclosed acute angle concerning the functional section. This spring arm section 23 may run straight up to concave within the altogether convex course of the restoring spring 12.

The spring arm section 23 extends up to a support section 24 over which the restoring spring 12 is supported altogether on the bottom of the housing 7. With reference to the section according to FIG. 2 the spring arm section 23 exceeds in this connection—starting from the connection area in the area of the pivot axis b—the middle axis a. Also the support section 24 may seat immediately on the housing bottom in the area of the middle axis a or also before this area.

In an elongation of the spring section 23 over the support section 24 there may result a second spring section 25 which is in cross section straight running which may include in the area of the support section 24 with the first spring section 23 an angle $\alpha$ of about 120 to 140°.

In an untensioned basic position according to the view in FIGS. 2 and 3 a support of the spring section 25 may be given over nearly the whole length of the spring section 25 on the housing bottom. Also the support may be given alone via the support section 24.

In the area of the free end of the spring section 25 facing away from the support section 24 and extending free from the support section 24 is mounted an engagement part 21 designed for engagement of the drive part 4.

According to another detail, the drive part 4 is realized in the form of a worm shaft, preferably a single-flight worm shaft. A helical pitch may be adapted to the spacing between two adjacent toothing projections of the counter wheel 2. The actual counting effect referred to one respective actuation can be adjusted due to this measure and due to the fact that the counter wheel is driven by a defined amount of a toothing projection during one revolution.

One respective driving projection 20, which may simultaneously also serve as a tooth for acting upon the engagement part 21, particularly can engage between two driving projections 20 and drive the counter wheel 2 during a rotation due to the helical or screw-like design.

The engagement part 21 is preferably realized on the restoring spring 12 and further preferably materially unified with the restoring spring 12. In view of the concave course K of the restoring spring 12 altogether the engagement part 21 is not regarded as part of the restoring spring.

Figure 6:
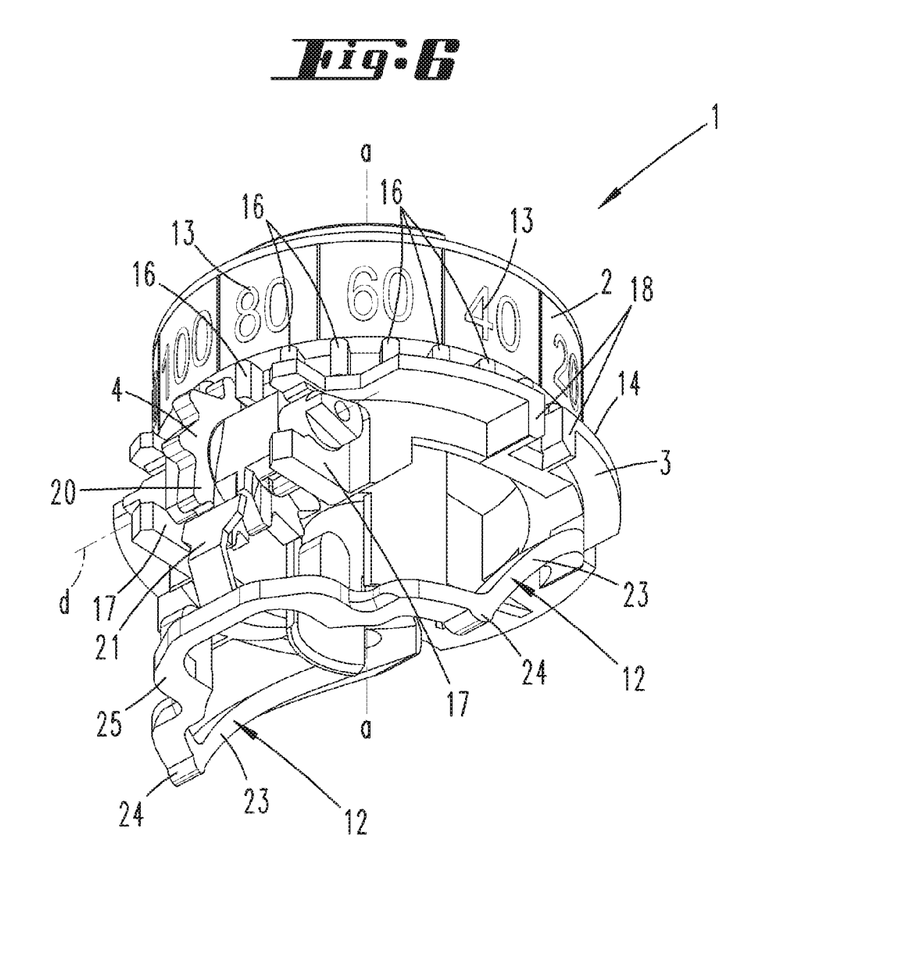
FIG. 6 shows the counter in a perspective single representation.

As it is moreover for example visible from FIG. 6, the engagement part 21 may be arranged on a region of the restoring spring which projects farest transverse to the rotational axis d and faresat away from the pivot axis b but once again preferably extending further cantilevered in the direction of the central axis a.

The engagement part 21 is in a cross section across to the middle axis a preferably designed similar to a blade that extends straight. A certain curved or bent formation may also be provided on the free end on the upper side of the engagement part 21 (see FIG. 3).

In the untensioned basic position shown in FIG. 3 results a greater distance c in direction of the longitudinal axis x viewed between the free end of the engagement part 21 and the pivot axis b of the restoring spring 12.

At an actuation of the handheld device 5, also at the shown embodiment upon a down pressing of the receptacle 6 in the direction of the press downward actuation P shown in the figures, via the seesaw-like design of the restoring spring 12 with its support on the housing bottom in the area of the support section 24, the engagement part 21 on the side of the spring arm end is raised essentially counter to the movement direction of the receptacle 6 and the counter mechanism 1, coming nearer to the drive part 4.

Figure 4:
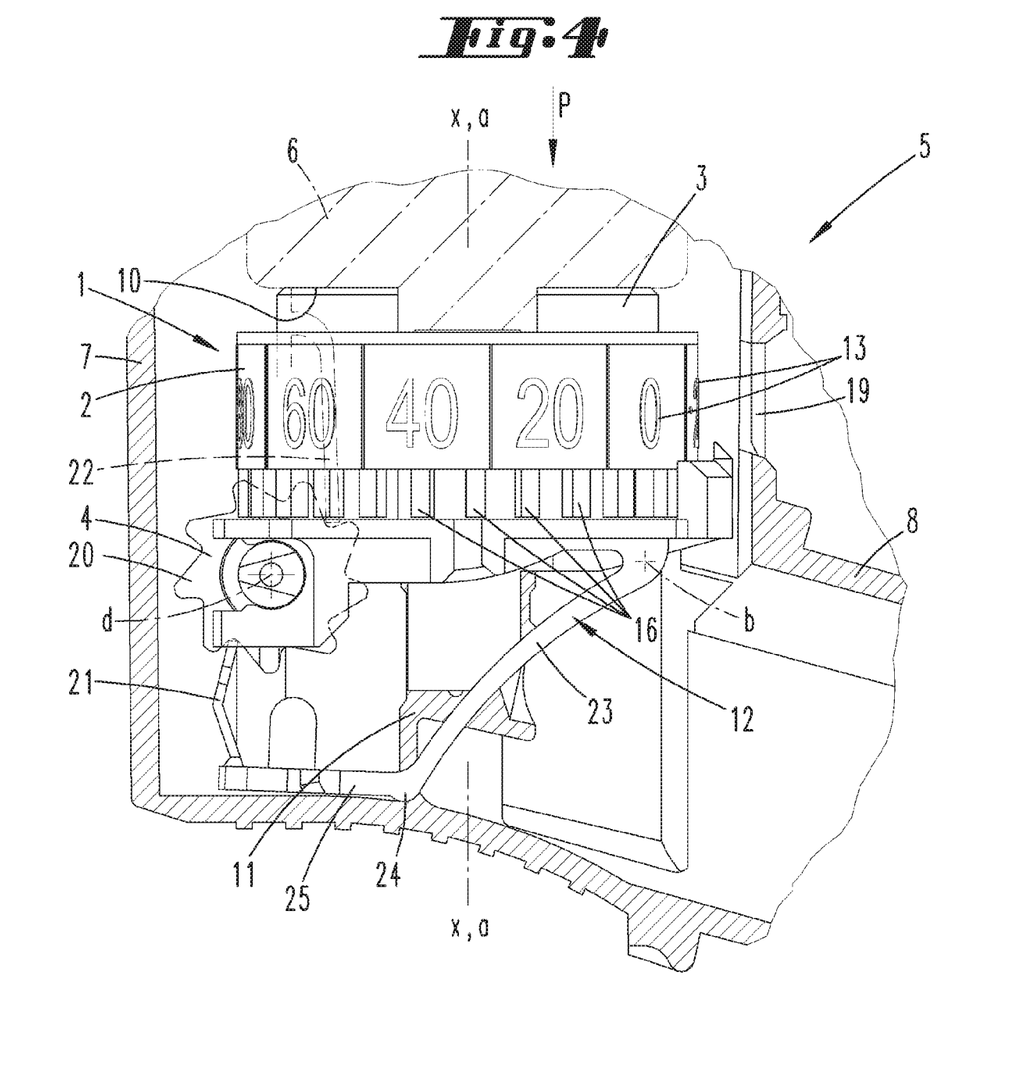
FIG. 4 shows a view corresponding to FIG. 3, related to an in between position during actuation of the handheld device.
Figure 5:
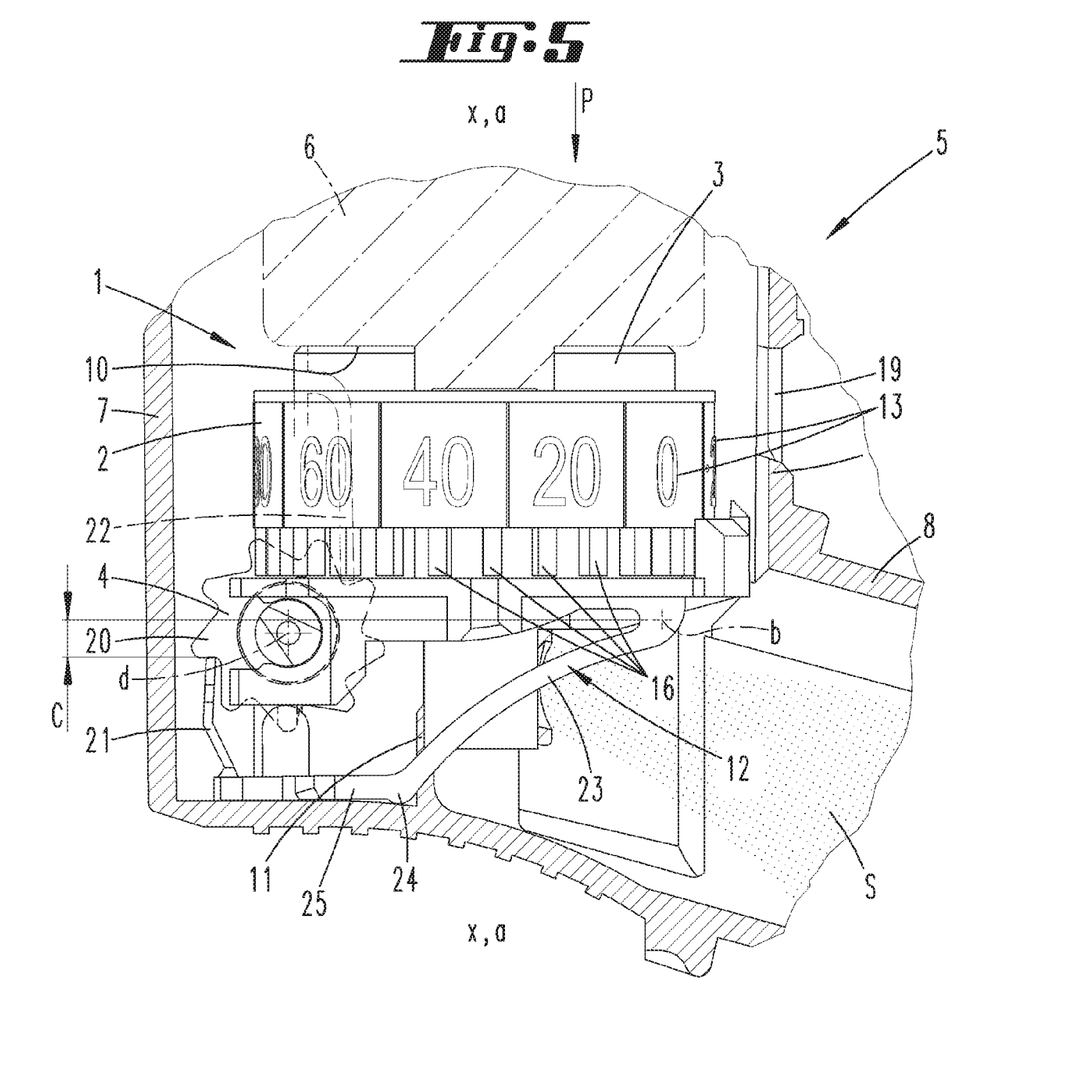
FIG. 5 shows a following representation concerning FIG. 4, concerning the actuation end position.

Upon an actuation of the handheld device 5 the engagement projection 21 meets a driving projection 20 of the driving part 4 and effects a turning of the worm-shaft around the pivot axis d of the drive part 4, even before a dispensing position of the receptacle 6 is reached (see FIGS. 4 and 5). The dispensing position means in this connection, especially in view of the shown embodiments, that a valve in the receptacle 6 is moved into an open position by the pressure actuation P and that such substance S may escape through the mouth piece out of the receptacle 6. In this position the smallest possible distance c between the free end of the engagement part 21 and the pivot axis b of the restoring spring 12 may result.

A backward rotation of the drive part 4 is simultaneously prevented by means of a locking part 22. The locking part 22 also interacts with the worm shaft, particularly with the toothing projections of the drive part 4 that form the helical design.

The drive part 4 interacts with the locking part 22 is on the opposite side of the corresponding interaction of the drive part 4 with the engagement part 21—referred to a side view according to FIG. 3, in which the rotational axis d of the drive part 4 forms a point.

The locking part 22 and the engagement part 21 are preferably directed oppositely. They may respectively consist of flat parts that extend in the direction of the central axis a and approximately parallel thereto. The engagement part 21 and/or the locking part 22 may also feature a hook-shaped formation on the upper side on the respective free end in order to promote the interaction with a driving projection 20.

The housing 7 of the handheld device may feature circumferentially distributed rib formations on its inner side. These rib formations 23 serve for securing the counter 1 against rotating. To this end, they may interact with the counter formations 18 on the mounting part 3. They may furthermore form a restricted guidance for the restoring spring 12.

Figure 9:
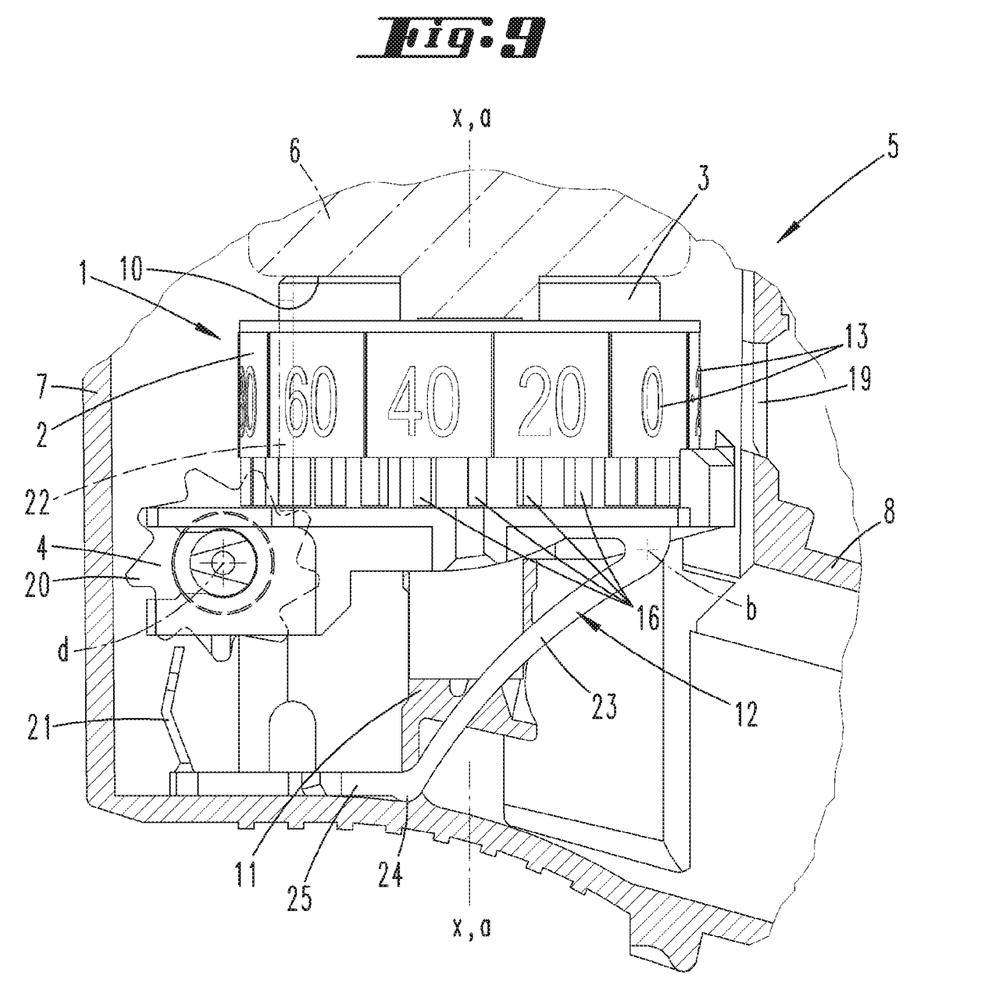
FIG. 9 shows a view corresponding to FIG. 3, concerning a second embodiment.

In FIG. 9 an alternative embodiment is shown at which the turning axis d of the drive part 4 runs outside of the counter wheel. This is given in view of a projection of the counter wheel 2 in the direction of the middle axis a of the counter wheel as well as in view of a projection of the turning axis d of the drive part cross directed to middle axis a.

As further will be aware from the drawings, the longitudinal axis x of the housing 7 and the middle axis a of the counter 1 coincide preferably in view of the counter 1 mounted in the housing 7.

The preceding explanations serve for elucidating all inventions that are included in this application and respectively enhance the prior art independently with at least the following combinations of characteristics, namely:

A handheld device, which is characterized in that upon force actuation first there is an effect on the counter wheel 2 of the counter 1 and thereafter the dispensing of the pharmaceutical substance.

A counter, which is characterized in that the restoring spring 12 is lever-like and does pivot upon actuation around a pivot axis b wherein in a cross section in which a largest distance between the engagement part 21 and the pivot axis b is given, the restoring spring 1ˆ2 has', seen from the counter 1, a concave course.

A counter which is characterized in that on the holding part 3 a locking part 22 is arranged for engagement to the driving part 4 and that the locking part 22 concerning the counter wheel 2 is provided for inside the holding part 3.

All the disclosed features (by themselves or combined with one another) are essential to the invention. The disclosure of the application herewith also includes the disclosure content of the appurtenant/appended priority documents (copy of the prior application) in their full content, also for the purpose of incorporating features of these documents in claims of the present application. The subclaims characterize with their features independent inventive further developments of the prior art, in particular in order to make divisional applications on the basis of these claims.

LIST OF REFERENCE SYMBOLS: (NOCH NICHT ÜBERARBEITET)

1 Counter
2 Counter wheel
3 Holding part
4 Drive part
5 Handheld device
6 Receptacle
7 Housing
8 Mouthpiece
9 Cap
10 Step surface
11 Receiving/dispensing stub
12 Restoring spring
13 Characters
14 Step surface
15 Bottom
16 Engagement toothing
17 Mounting formation
18 Counter formations
19 Window
20 Driving projection
21 Engagement part 22 Locking part
23 Spring section
24 Support section
25 Spring section
a middle axis
b pivot axis
c Distance
d Turning axis
x longitudinal axis
K Concave course
P Force actuation
S Substance
α angle

The invention claimed is:

1. A handheld device for dispensing a pharmaceutical substance, comprising:
 a housing;
 a receptacle disposed in the housing and containing the pharmaceutical substance and being configured for dispensing the pharmaceutical substance upon pressure activation after going through a predetermined displacement path against a spring arranged in the receptacle, and
 a counter having a counter wheel that turns based on movement of the receptacle in the displacement path, wherein the counter comprises a driving part for turning the counter wheel and a holding part on which the counter wheel is rotatably arranged, the receptacle also moving the counter longitudinally along a direction of a longitudinal axis of the housing when moving in the displacement path during dispensing of the pharmaceutical substance, and
 a restoring spring configured for a back movement of the counter after an actuation of the receptacle, the restoring spring having an engagement part for cooperation with the driving part,
 wherein the holding part is independent from the housing and the driving part is arranged immediately on the holding part, wherein upon force actuation the counter wheel is turned and the pharmaceutical substance is dispensed thereafter,
 wherein the restoring spring runs in a direction of a longitudinal axis thereof below the counter, between the counter and a bottom of the housing and
 wherein a linear shift of one section of the restoring spring causes a movement at the same time in an opposite direction of another section of the restoring spring having the engagement part, whereby the engagement part on a side of a spring arm end is raised essentially opposite to a direction of movement of the receptacle and the counter upon a pressing downward of the receptacle, and approaches the driving part.

2. A counter for a handheld device having a housing and a receptacle for dispensing a pharmaceutical substance, the counter comprising:
 at least one counter wheel having readable characters and being configured to be longitudinally movable along longitudinal axis of the housing by movement of the receptacle during dispensing of the pharmaceutical substance when the counter is arranged in the housing,
 a driving part configured for turning the counter wheel,
 a restoring spring configured for a back movement of the counter after an actuation of the receptacle, the restoring spring having an engagement part for cooperation with the driving part,
 wherein the restoring spring is lever-like and pivots upon actuation around a pivot axis, wherein in a cross section in which a largest distance between the engagement part and the pivot axis is given, the restoring spring has, seen from the counter, a concave course,
 wherein the restoring spring runs in a direction of a longitudinal axis thereof below the counter, between the counter and a bottom of the housing, and
 wherein a linear shift of one section of the restoring spring causes a movement at the same time in an opposite direction of another section of the restoring spring having the engagement part, whereby the engagement part on a side of a spring arm end is configured to be raised essentially opposite to a linear direction of movement of the counter upon a pressing downward of the receptacle, and approaches the driving part.

3. The counter according to claim 2, further comprising a locking part configured for engagement with the driving part, wherein the locking part is disposed inside a holding part of the counter.

* * * * *